US012432069B2

United States Patent
Wu (10) Patent No.: US 12,432,069 B2
(45) Date of Patent: Sep. 30, 2025

(54) BLOCKCHAIN-BASED ELECTRONIC MEDICAL RECORD SHARING METHOD AND ELECTRONIC DEVICE

(71) Applicant: Xi'an Creation Keji CO., Ltd., Xi'an (CN)

(72) Inventor: Conghua Wu, Xi'an (CN)

(73) Assignee: XI'AN CREATION KEJI CO., LTD., Xi'an (CN)

(*) Notice: Subject to any disclaimer, the term of this patent is extended or adjusted under 35 U.S.C. 154(b) by 153 days.

(21) Appl. No.: 17/256,898

(22) PCT Filed: Dec. 26, 2020

(86) PCT No.: PCT/CN2020/139753
§ 371 (c)(1),
(2) Date: Dec. 29, 2020

(87) PCT Pub. No.: WO2022/134119
PCT Pub. Date: Jun. 30, 2022

(65) Prior Publication Data
US 2025/0047498 A1    Feb. 6, 2025

(51) Int. Cl.
*H04L 9/32* (2006.01)
*G16H 10/60* (2018.01)
*H04L 9/00* (2022.01)
*H04L 9/08* (2006.01)

(52) U.S. Cl.
CPC .......... *H04L 9/3247* (2013.01); *G16H 10/60* (2018.01); *H04L 9/0825* (2013.01); *H04L 9/3236* (2013.01); *H04L 9/50* (2022.05)

(58) Field of Classification Search
CPC ............... H04L 9/3247; H04L 9/0825; H04L 9/3236; H04L 9/50; H04L 9/3239; H04L 2209/88; G16H 10/60
See application file for complete search history.

(56) References Cited

FOREIGN PATENT DOCUMENTS

| CN | 109670334 A | * | 4/2019 |
| CN | 112614557 A | * | 4/2021 |

* cited by examiner

*Primary Examiner* — Jeffrey C Pwu
*Assistant Examiner* — Mayasa A. Shaawat
(74) *Attorney, Agent, or Firm* — WPAT, PC (57) ABSTRACT

A blockchain-based electronic medical record sharing method for a medical institution node is provided. The method includes: obtaining an electronic medical record from a preset database; performing a Hash operation on the electronic medical record to generate a medical record abstract; constructing a GRS code based on a finite field; generating a public key and a private key according to the GRS code; processing the medical record abstract with the private key to obtain a first digital signature; decoding the first digital signature with the private key to obtain an error vector as a second digital signature; sending the second digital signature to a verification node for verification; and receiving a block confirmed by the verification node and adding the block to a blockchain structure maintained by the preset database.

8 Claims, 6 Drawing Sheets

BLOCKCHAIN-BASED ELECTRONIC MEDICAL RECORD SHARING METHOD AND ELECTRONIC DEVICE

TECHNICAL FIELD

The disclosure relates to the field of blockchain technologies, and more particularly to a blockchain-based electronic medical record sharing method and an electronic device.

BACKGROUND

An EMR (Electronic Medical Record) is also called a computerized medical record system or a computer-based patient record. It is a digital medical record saved, managed, transmitted and reproduced by an electronic device (computer, health card, etc.), instead of a handwritten medical record. It includes all information of a paper medical record, and compared with a paper medical record, the electronic medical record also has significances of providing complete, real-time, anytime and anywhere access to patient information for medical staff, as well as supporting the sharing of the medical information while the patient in different medical institutions.

However, existing medical institutions that use electronic medical records usually only store the electronic medical records for future custody and inquiry, and the electronic medical records among different medical institutions cannot be shared. As a result, a patient cannot easily access the electronic medical record of the original medical institution when they visit other medical institutions. And since each medical institution manages its own electronic medical record, there is a risk that the electronic medical record may be tampered with, so the authenticity of the electronic medical record cannot be guaranteed.

SUMMARY

In view of the above issues in the related art, the disclosure provides a blockchain-based electronic medical record sharing method and an electronic device. The technical problem to be solved by the disclosure is realized by the following technical solutions.

The technical solutions of the disclosure are described as follows.

According to one aspect of the disclosure, a blockchain-based electronic medical record sharing method adapted for a medical institution node, includes steps of: obtaining to an electronic medical record from a preset database; performing a Hash operation on the electronic medical record to generate a medical record abstract; constructing a GRS (Generalized Reed-Solomon) code based on a finite field; generating a public key and a private key according to the GRS code; using the private key to process the electronic medical record abstract to thereby obtain a first digital signature; decoding the first digital signature with the private key to obtain an error vector as a second digital signature; sending the second digital signature to a verification node for verification; and receiving a block confirmed by the verification node and adding the block to a blockchain structure maintained by the preset database.

According to an embodiment of the disclosure, the step of constructing a GRS code based on a finite field, includes: constructing the finite field, and constructing the GRS code with a code length of n, a dimensionality of k and an error correction capability of t according to the finite field, where n, k and t are arbitrary positive integers and satisfy $$t = \left\lfloor \frac{n-k}{2} \right\rfloor.$$

According to an embodiment of the disclosure, the step of generating a public key and a private key according to the GRS code, includes: selecting a nonsingular matrix of $(n-k) \times (n-k)$, a dense matrix of $n \times n$ and a sparse matrix of $n \times n$ in the finite field; wherein a rank of the dense matrix is z, and an average row weight and an average column weight of the sparse matrix are x; where z and x are natural numbers, z is less than n and x is less than n; performing a matrix addition operation on the dense matrix and the sparse matrix to obtain a transformation matrix; performing a matrix multiplication operation on an inverse matrix of the nonsingular matrix, a check matrix and a transpose matrix of the transformation matrix to obtain the public key, wherein the check matrix is a $(n-k) \times n$ matrix of the GRS code; and taking the nonsingular matrix, the check matrix, the transformation matrix and a decoding algorithm as the private key.

According to an embodiment of the disclosure, the step of performing a Hash operation on the electronic medical record to generate a medical record abstract includes: performing a first Hash operation on the electronic medical record; and performing a second Hash operation on a result obtained by the first Hash operation to obtain the electronic medical record abstract.

According to an embodiment of the disclosure, the step of using the private key to process the electronic medical record abstract to thereby obtain a first digital signature includes: performing a multiplication operation on the nonsingular matrix and the electronic medical record abstract to obtain the first digital signature.

According to an embodiment of the disclosure, the step of decoding the first digital signature with the private key to obtain an error vector as a second digital signature, includes: decoding the first digital signature with the decoding algorithm in combination with the transformation matrix of the private key to obtain a first error vector; performing a matrix multiplication operation on the first error vector and an inverse matrix of the transformation matrix of the private key to obtain a second error vector, wherein a weight of the second error vector is less than or equal to a value of error correction capability of the GRS code; and obtaining the second digital signature by using the second error vector.

According to an embodiment of the disclosure, the blockchain-based electronic medical record sharing method further includes: after obtaining the second error vector, constructing an index pair of the second error vector; and taking the index pair of the second error vector as the second digital signature accordingly.

According to another aspect of the disclosure, a blockchain-based electronic medical record sharing method adapted for a verification node, includes steps of: receiving a second digital signature from a medical institution node, wherein the second digital signature is obtained by steps of: obtaining to an electronic medical record from a preset database; performing a Hash operation on the electronic medical record to generate a medical record abstract; constructing a GRS (Generalized Reed-Solomon) code based on a finite field; generating a public key and a private key according to the GRS code; using the private key to process the electronic medical record abstract to thereby obtain a first digital signature; and decoding the first digital signature with the private key to obtain an error vector as the second digital signature; obtaining the public key from the medical institution node and verifying the second digital signature according to the public key; encapsulating the electronic medical record abstract into a block when the second digital signature is verified to be valid; and confirming the block through a consensus mechanism, and sending the block as confirmed to the medical institution node.

According to an embodiment of the disclosure, the step of obtaining the public key from the medical institution node and verifying the second digital signature according to the public key includes: receiving the public key from the medical institution node, processing the second digital signature by using the public key to obtain a to-be-verified medical record abstract; obtaining the electronic medical record and performing a Hash operation on the electronic medical record to obtain a target electronic medical record abstract; and comparing the to-be-verified electronic medical record abstract with the target electronic medical record abstract, the verifying succeeds if the to-be-verified electronic medical record abstract is the same as the target electronic medical record abstract, otherwise the verifying fails.

According to still another aspect of the disclosure, an electronic device, includes a processor, a communication interface, a memory and a communication bus; the processor, the communication interface and the memory are mutually communicated with one another via the communication bus; the memory is configured for storing a computer program; and the processor is configured for executing the computer program stored in the memory to carry out the blockchain-based electronic medical record sharing method methods of the above embodiments.

Based on blockchain and digital signature technologies, the disclosure can ensure that the electronic medical record can be shared among various medical institutions without being tampered with. Moreover, the digital signature solution is highly feasible, which can reduce public key quantity, improve the signature efficiency, and further improve the security.

The disclosure will be further described in detail with reference to drawings and embodiments.

DETAILED DESCRIPTION OF EMBODIMENTS

Technical solutions of embodiments of the disclosure will be clearly and fully described in the following with reference to the accompanying drawings in the embodiments of the disclosure. Apparently, the described embodiments are some of the embodiments of the disclosure, but not all of the embodiments. All other embodiments obtained by skilled person in the art based on the described embodiments of the disclosure are within the scope of protection of the instant application.

The disclosure will be further described in detail in combination with specific embodiments, but the implementation mode of the disclosure is not limited to this.

In order to solve the problem that the existing electronic medical records cannot be shared among different medical institutions and have the risk of being tampered with, the embodiments of the disclosure provide a blockchain-based electronic medical record sharing method and an electronic device.

Firstly, a blockchain-based electronic medical record sharing method provided by the embodiment of the disclosure is adapted for a medical institution node. The electronic medical record sharing method is described below.

Figure 1:
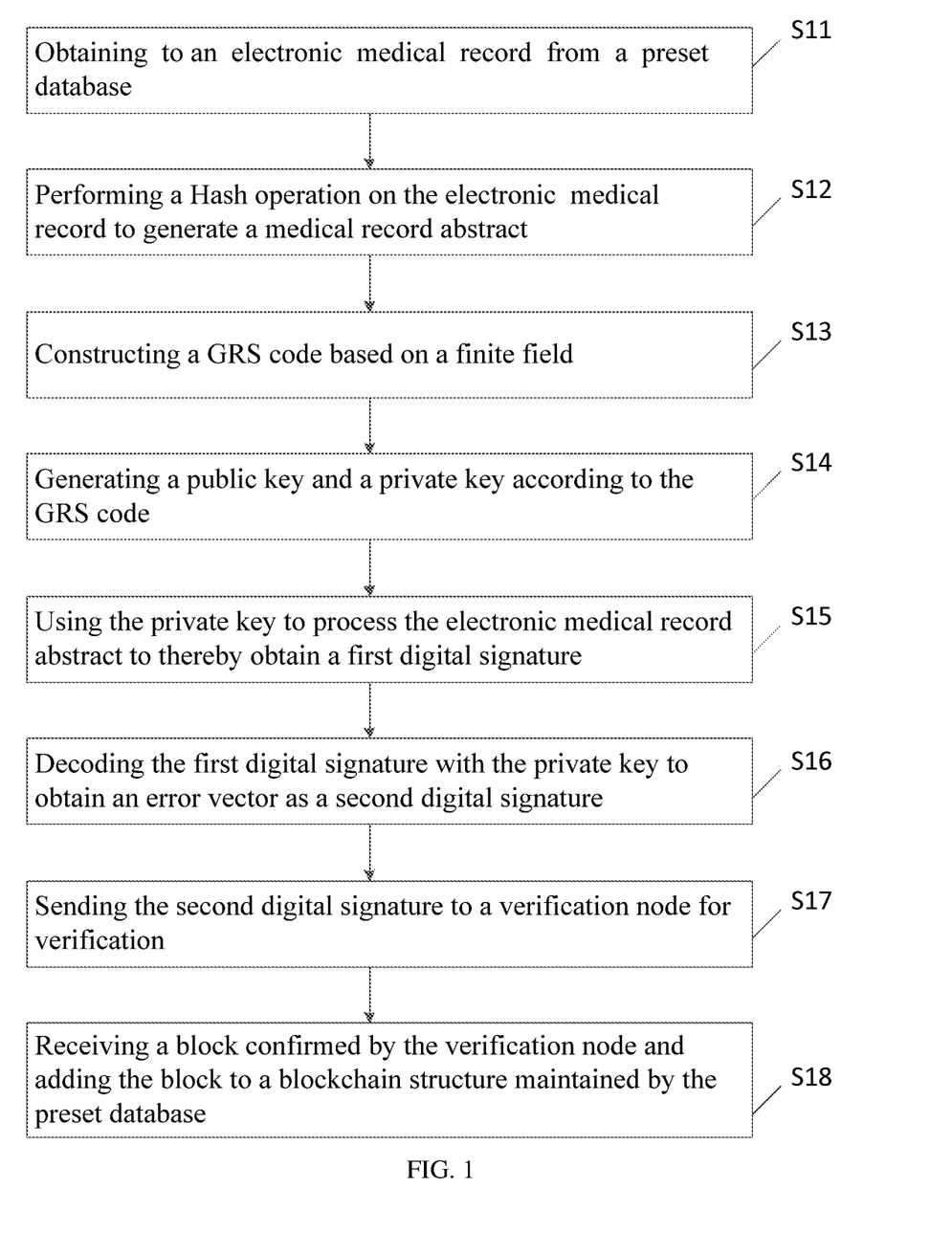
FIG. 1 is a schematic flowchart of a blockchain-based electronic medical record sharing method according to an embodiment of the disclosure.

Referring to FIG. 1, it is a schematic flowchart of a blockchain-based electronic medical record sharing method according to the embodiment of the disclosure. The blockchain-based electronic medical record sharing method is adapted for a medical institution node. The medical institution node may be a computing server of a medical institution, and a blockchain is maintained by each node server together, and the medical institution node is one of many nodes. The blockchain-based electronic medical record sharing method includes steps of:

S11, obtaining to an electronic medical record from a preset database.

Medical institution refers to hospital, clinic, community health center and other medical organization. The EMR is medical record information recorded by doctors of medical institutions in the process of asking patient, such as symptoms and treatment methods. The medical record information is stored in a preset database of each medical institution, and can be directly obtained from the preset database while using.

S12, performing a Hash operation on the electronic medical record to generate a medical record abstract.

Hash operation refers to an algorithm that can map a message of any length into a message of a fixed length. The hash operation in the disclosure can adopt any one of MD4, MD5 or SHA256. A medical record abstract is an unencrypted plaintext, which includes character(s) that can be directly understood. A plaintext of any length is mapped into a string of ciphertext of fixed length by performing a first encryption with a hash algorithm. The ciphertext is an encrypted string, which cannot be understood directly. This string of ciphertext is a digital abstract. In this step, the electronic medical record abstract is generated by the plaintext of the electronic medical record through the hash operation which is used for a next encryption of the electronic medical record.

In an optional implement, S12 may include S121 to S122.

S121, performing a first hash operation on the electronic medical record that needs a digital signature.

If M is a plaintext of EMR, h(M) is obtained by performing the first Hash operation on the electronic medical record.

S122, performing a second Hash operation on a result obtained by the first Hash operation to obtain the electronic medical record abstract.

In this step, performing a second Hash operation on the result h(M) of the first Hash operation to obtain the EMR abstract $S_x$, that is, $S_x = h(h(M)|i)$, where $i = 0, 1, 2, \ldots$. In this embodiment of the disclosure, i=0, so that the electronic medical record abstract $S_x$ is a vector with a length of n−k.

In other embodiments, one or more Hash operation(s) can be performed to obtain the EMR abstract, which can satisfy an output with a fixed length.

S13, constructing a GRS (Generalized Reed-Solomon) code based on a finite field.

For example, this step may include: constructing the finite field, and constructing the GRS code with a code length of n, a dimensionality of k and an error correction ability of t according to the finite field, where n, k and t are arbitrary positive integers and satisfy $$t = \left\lfloor \frac{n-k}{2} \right\rfloor.$$

The finite field $F_q$ with q elements can be selected, and a positive integer m is selected to satisfy $q=2^m$.

It should be noted that the reason why the finite field $F_q$ is selected in this embodiment of the disclosure instead of a conventional binary system is that, while facing an attack of ISD decoding, with the same security level of codes (such as Goppa code), a public key quantity of Goppa codes based on the finite field $F_q$ is smaller than those of Goppa codes based on binary. For example, the public key quantity of Goppa codes based on the finite field with a security level of 128 is 725740 bits; the public key quantity of binary Goppa codes with a security level of 128 is 1537536 bits. In contrast, the public key quantity of Goppa codes based on the finite field $F_q$ is about one order of magnitude smaller than that of Goppa codes based on binary.

In addition, the GRS code is chosen instead of other code (such as Goppa code), because the GRS code is a maximum distance separable (MDS) code with good performance, and the GRS code has applied in various fields and has good practicability. Besides, the GRS code is more flexible than Goppa code; and GRS code has an advantage of stronger expansibility.

S14, generating a public key and a private key according to the GRS code.

The public key and the private key are generated according to the GRS code, which can ensure that the public key and private key have higher security performance and occupy less space, and generate different public keys and private keys for different logistics information. One public key can decrypt only one encrypted label.

In an optional embodiment, S14 may include S141 to S144.

S141, selecting a nonsingular matrix of (n−k)×(n−k), a dense matrix of n×n and a sparse matrix of n×n in the finite field; and a rank of the dense matrix is z, and an average row weight and an average column weight of the sparse matrix are x; where z and x are natural numbers, z is less than n and x is less than n.

As an embodiment of the disclosure, the rank z of the dense matrix is far less than n, and the average row weight and average column weight x of the sparse matrix are far less than n.

Specifically, a dense matrix can be expressed by a product of a transposed matrix of a matrix and the matrix itself, that is $\vec{a}^T \cdot \vec{b}$, and $\vec{a}$, $\vec{b}$ are two z×n matrices defined on the finite field $F_q$, and the ranks of the matrices are z.

Optional, there are several choices for the selection of parameters m, n, k, t and x for reference in the solutions of the disclosure. Referring to Table 1, there are several choices and not limited to these. However, considering the correctness, feasibility and security of the solution, as well as the public key quantity and signature length, the three groups of parameter values listed in Table 1 are preferably adopted in the solutions of the disclosure.

TABLE 1

| Parameters Selection | | | | |
|---|---|---|---|---|
| m | n | k | t | x |
| 12 | 4094 | 4074 | 10 | 1~1.1 |
| 16 | 65534 | 65516 | 9 | 1~1.1 |
| 10 | 1022 | 1002 | 10 | 1~1.1 |

S142, performing a matrix addition operation on the dense matrix and the sparse matrix to obtain a transformation matrix.

Specifically, a formula (1) is used for the matrix addition operation:

$$\vec{Q} = \vec{R} + \vec{T} \quad (1)$$

Where $\vec{Q}$ represents the transformation matrix, $\vec{R}$ represents the dense matrix, $\vec{T}$ represents the sparse matrix.

S143, performing a matrix multiplication operation on an inverse matrix of the nonsingular matrix, a check matrix and a transpose matrix of the transformation matrix to obtain the public key, and the check matrix is a (n−k)×n matrix of the GRS code.

Specifically, the multiplication operation satisfies a formula (2):

$$\vec{H}' = \vec{S}^{-1} \cdot \vec{H} \cdot \vec{Q}^T \quad (2)$$

Where $\vec{H}'$ represents the public key, $\vec{S}^{-1}$ represents the inverse of the nonsingular matrix, $\vec{H}$ represents the check matrix, $\vec{Q}^T$ represents the transpose matrix of the transformation matrix.

S144, taking the nonsingular matrix, the check matrix, the transformation matrix and a decoding algorithm as the private key.

Understandably, the public key is used for public, and the private key is used for storage. The public key and the private key are two different parameter sets in an algorithm, but they are internally related. The public key and the private key are generated at the same time, but they can be used independently.

S15, using the private key to process the electronic medical record abstract to thereby obtain a first digital signature.

For example, this step may include:

Performing a multiplication operation on the nonsingular matrix and the electronic medical record abstract, and obtaining the first digital signature. Specifically, the multiplication operation satisfies a formula (3):

$$S'_x = \vec{S} \cdot S_x \quad (3)$$

Where $S'_x$ represents the first digital signature, which can also be called a to-be-decoded corrector, $\vec{S}$ represents the nonsingular matrix, $S_x$ represents the electronic medical record abstract.

S16, decoding the first digital signature with the private key and taking an obtained error vector as a second digital signature.

For example, this step may include S161 to S163.

S161, decoding the first digital signature with the decoding algorithm in combination with the transformation matrix of the private key to obtain a first error vector.

The decoding algorithm can be anyone of the existing decoding algorithms. In this embodiment, the decoding algorithm is preferably an iterative decoding algorithm in time domain, that is, a combination of BM (Berlekamp-Massey) iterative decoding algorithm, Qian shi search algorithm (Chien) and Forney algorithm. The decoding algorithm is fast, easy to implement and easy to be implemented by computer, so it is a fast decoding algorithm.

Alternatively, the decoding algorithm may include the following steps:

Step 1: calculating a corrector;
Step 2: determining an error location polynomial;
Step 3: determining an error estimation function;
Step 4: solving a number of wrong positions and an error value, and correcting the number of wrong positions and the error value.

The above four steps are completed means that one decoding completed. If the decoding succeeds, an error vector will be directly decoded; otherwise, it will be regarded as decoding failure.

According to the solutions of the embodiment of the disclosure, if the decoding fails, i'=i+1, and a first error vector is obtained by performing a hash operation again and decoding again, and until the decoding succeeds.

S162, performing a matrix multiplication operation on the first error vector and an inverse matrix of the transformation matrix of the private key to obtain a second error vector, and a weight of the second error vector is less than or equal to a value of the error correction capability of the GRS code.

Specifically, the matrix multiplication operation in this step may satisfy a formula (4):

$$\bar{e} = \vec{e} \cdot \vec{Q}^{-1} \quad (4)$$

Where $\bar{e}$ represents the second error vector, $\vec{e}$ represents the first error vector, $\vec{Q}^{-1}$ represents the inverse matrix of the transformation matrix of the private key.

S163, obtaining the second digital signature by using the second error vector.

So far, the digital signature based on error correction code of error vector has been obtained, but the error vector occupies more bits due to the existence of a plurality of 0 elements. In order to reduce the bit number of the error vector, on the basis of the above embodiment, it can be further optimized by solutions provided of the disclosure.

Preferably, the method further includes the following steps:

After obtaining the second error vector, constructing an index pair of the second error vector.

Specifically, the index pair of the second error vector can be obtained according to a formula (5).

$$I_e = \sum_{j=1}^{t_p} \binom{\alpha_j}{c_j} = \binom{\alpha_1}{c_1} + \binom{\alpha_2}{c_2} + \ldots + \binom{\alpha_{t_p}}{c_{t_p}} \quad (5)$$

Where $I_e$ represents the index pair.

In other words, the non-zero elements in the second error vector are extracted and marked as the error values, and the index pair of the second error vector $I_e$ is constructed with error positions α and wrong locations c.

Accordingly, the index pair is used as a digital signature.

It should be noted that, a signature usually corresponds to a process of signature verification. As a step of generating only a digital signature, the index pair $I_e$ obtained will be used as a digital signature. However, in the process of a signature verification, due to the digital signature with the index pair $I_e$ and the electronic medical record abstract h(h(m)|i) will be verified by a signer, therefore, after the verification succeeds, [$I_e$|i] will be taken as the digital signature of EMR plaintext M.

In a preferred solution, the bit number and the length of the signature can be reduced by constructing an index pair on the obtained second error vector and taking the index pair as a digital signature.

S17, sending the second digital signature to a verification node for verification.

After obtaining the second digital signature, the digital signature and EMR abstract need to be broadcast to each verification node in the network. After receiving the digital signature and EMR abstract, a verification node verifies the digital signature. The specific verification method can refer to the blockchain-based electronic medical record sharing method adapted for a verification node in the second embodiment of the disclosure. In order to avoid duplication, it is omitted here.

S18, receiving a block confirmed by the verification node and adding the block to a blockchain structure maintained by the preset database.

Each node maintains a common blockchain, and each node stores the blockchain distributed. Therefore, a common blockchain is also maintained in the default database. After receiving the block confirmed by the verification node, the confirmed block is connected with the previous block in the local blockchain structure according to the occurrence order to update the maintained blockchain, thus realizing electronic medical records sharing.

It should be noted that, the solutions of the disclosure is realized based on the blockchain technology. The blockchain is a brand-new method that uses block chain data structure to verify and store data, uses distributed node consensus algorithm to generate and update data, uses cryptography to ensure the security of data transmission and access, and uses intelligent contract composed of automatic script code to program and operate data. It has the characteristics of decentralization, openness and unforgeability.

The blockchain-based electronic medical record sharing method provided by the embodiment of the disclosure is adapted for a medical institution node. The public key and private key are generated by GRS code of the finite field $F_q$, the electronic medical record abstract is obtained according to the electronic medical record, the electronic medical record abstract is processed by the private key to obtain the digital signature, the digital signature is encapsulated into the block, and the block is confirmed through the consensus mechanism and sent to the medical institution node. Based on blockchain and digital signature technologies, the disclosure can ensure that the electronic medical record can be shared among various medical institutions without being tampered with. Moreover, the digital signature solution is highly feasible, which can reduce the public key quantity; improve the signature efficiency, as well as the security.

In the second aspect, a blockchain-based electronic medical record sharing method adapted for a verification node is provided in the embodiment of the disclosure. The blockchain-based electronic medical record sharing method is described below.

Figure 2:
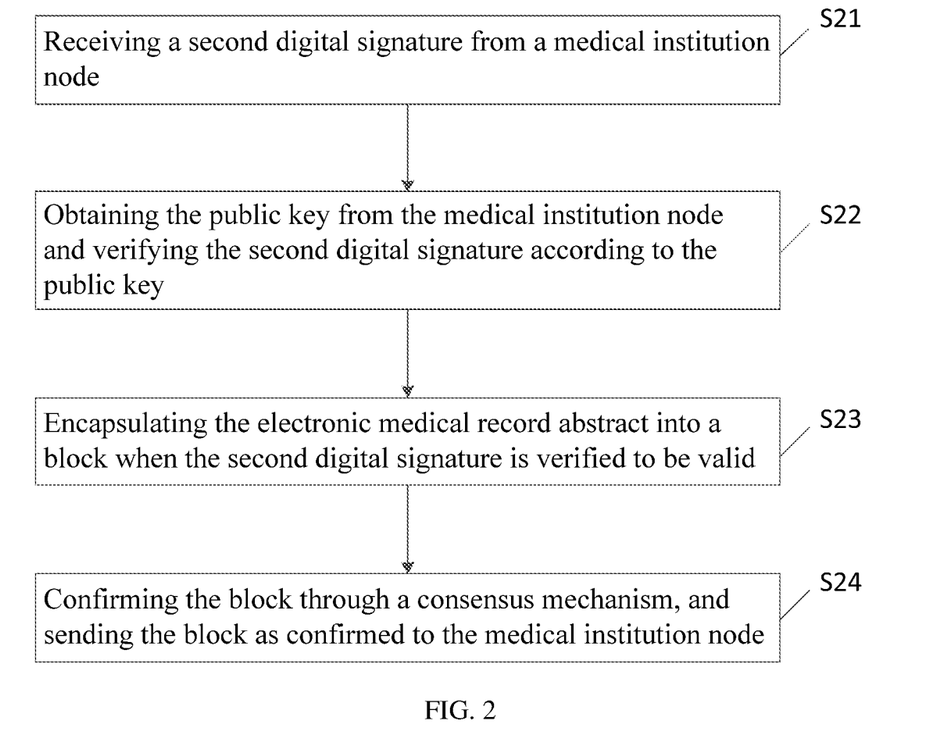
FIG. 2 is a schematic flowchart of another blockchain-based electronic medical record sharing method according to an embodiment of the disclosure.

Referring to FIG. 2, it is a schematic flowchart of another blockchain-based electronic medical record sharing method provided in the embodiment of the disclosure. The schematic flowchart of the blockchain-based electronic medical record sharing method provided in the embodiment of the disclosure is adapted for the verification node.

First of all, it should be noted that, due to a digital signature process and a signature verification process are corresponding processes, the verification process in this part is a signature verification process of the digital signature provided by the medical institution node in the first aspect.

The blockchain-based electronic medical record sharing method includes:

S21, receiving a second digital signature from a medical institution node, where the second digital signature is obtained by the blockchain-based electronic medical record sharing method in the first aspect above of the embodiment.

In this step, the verification node receives a digital signature and an EMR abstract broadcast from a medical institution node in the network for a further verification.

S22, obtaining the public key from the medical institution node and verifying the second digital signature according to the public key.

Since the public key of each node is public, the public key is obtained from the medical institution node. Verifying the digital signature through the obtained public key, it can be proved that the EMR abstract comes from the medical institution node and the EMR abstract is complete and not be tampered with.

For example, this step may include S221 to S223:

S221, receiving the public key from the medical institution node, processing the second digital signature by using the public key to obtain a to-be-verified electronic medical record abstract.

Corresponding to the solution of taking the second error vector as the digital signature mentioned above, the public key is used directly to process the second error vector to obtain the to-be-verified electronic medical record abstract in this step.

Corresponding to the solution of taking the index pair as the digital signature mentioned above, the second error vector is recovered according to the index pair, and the public key is used to process the second error vector to obtain the to-be-verified electronic medical record abstract in this step.

Specifically, recovering the second error vector according to the index pair, that is, the location of the index $\alpha_j$ in the index pair $I_e$ is filled with $c_j$, the other location except the index $\alpha_j$ of the index pair $I_e$ is filled with 0, until the length of the vector $\vec{e}$ is (n−k).

The public key is used to process the second error vector, that is, according to a formula (6), the to-be-verified electronic medical record abstract is obtained:

$$y = \vec{H}' \cdot \vec{e}^T \quad (6)$$

Where y represents the to-be-verified electronic medical record abstract.

Computing a product of a value of a corresponding row indexed according to the index $\alpha_j$ in each column of the public key $\vec{H}'$ and $c_j$, and taking the product as the EMR abstract.

S222, obtaining the electronic medical record and performing a Hash operation on the electronic medical record to obtain a target electronic medical record abstract.

Similarly, the target electronic medical record needs to be hashed twice. The specific steps are the same as those in the first aspect, and it will not be repeated here. Through two hash operations, the target electronic medical record abstract y'=h(h(M)|i) is obtained.

S223, comparing the to-be-verified electronic medical record abstract with the target electronic medical record abstract, the verification succeeds if the to-be-verified electronic medical record abstract is the same as the target electronic medical record abstract, otherwise the verification fails.

In the embodiment of the disclosure, the to-be-verified electronic medical record abstract y is compared with the target EMR abstract y', if y=y', that is, if the to-be-verified electronic medical record abstract is equal to the target electronic medical record abstract, the verification signature succeeds; otherwise, the verification signature fails.

S23, encapsulating the electronic medical record abstract into a block when the second digital signature is verified to be valid.

The block is the data block that records the electronic medical record abstract, including a block header and a block body. The block body is used to store the electronic medical record abstract. The block header includes a hash value, a timestamp, a version number, a difficulty value, a random number and a Merkel tree rooting of a previous block. A Merkel tree is a Middle binary tree, which is composed of a root node, intermediate nodes and leaf nodes. The Leaf node stores a data and a hash value of the data. An intermediate node is a hash value of a leaf node, while a root node is a hash value of an intermediate node, which is called Merkel rooting. Data change of any node will lead to a change of the Merkel rooting, so it can sum up data and verify the integrality of the data through the Merkel tree. The time stamp refers to a time mark used to prove the occurrence time of the electronic medical record abstract; the difficulty value refers to the difficulty of confirming the validity of a block; the random number is the parameter used to calculate the hash value.

S24, confirming the block through a consensus mechanism, and sending the block as confirmed to the medical institution node.

The consensus mechanism refers to a mean for a node in the network to how to reach consensus and confirm effectiveness of a block, which mainly includes workload proving mechanism, equity proving mechanism and share authorization proving mechanism. In this embodiment, the workload proving mechanism is adopted. The workload proving mechanism refers to a kind of workload proof, which means that nodes spend a lot of computing power of a computer to meet requirements. The proving is very easy to verify. When a node completes a workload certification, the other nodes can quickly verify the validity. Specifically, firstly, a hash value of the block header composed of a hash value, a timestamp, a version number, a difficulty value, a random number and a Merkel tree rooting of a previous block is calculated according to a hash algorithm. In this embodiment, SHA256 is adopted as the hash algorithm; then, a target value is calculated according to the difficulty value, and the target value=the maximum target value/the difficulty value, wherein, the maximum target value is a constant value, and the difficulty value is determined by the difficulty of the blockchain confirmation maintained by a blockchain system. Then the hash value of the block header is compared with the target value. If the hash value of the block header is less than or equal to the target value, the block is confirmed to be valid. If the hash value of the block header is greater than the target value, the random number in the block header will be added by one, and the hash value of the block head will be calculated again. The hash value of the block head recalculated is compared with the target value again. The above process is repeated until the hash value of the block header is less than or equal to the target value, so as to complete the workload calculation of the block; finally, a hash operation is performed by another verification node on the final block header in the above process to quickly verify, so as to complete the block confirmation. After the block confirmation is completed, it is broadcast to the network. After receiving the block confirmed by the verification node, the medical institution node in the network can add the block confirmed to the blockchain.

The blockchain-based electronic medical record sharing method provided by the embodiment of the disclosure is adapted for the verification node. The public key and the private key are generated by the GRS code based on the finite field $F_q$, the electronic medical record abstract is obtained according to the electronic medical record, the electronic medical record abstract is processed with the private key to obtain the digital signature, and the digital signature is encapsulated into the block, and the block is confirmed and verified through the consensus mechanism. Based on blockchain and digital signature technologies, the solution of the disclosure can ensure that the electronic medical record can be shared among various medical institutions without being tampered with. Moreover, the digital signature solution provided in this disclosure is highly feasible, which can reduce public key quantity, improve the signature efficiency, and further improve the security.

Thirdly, an electronic device is further provided in the embodiment of the disclosure.

Figure 3:
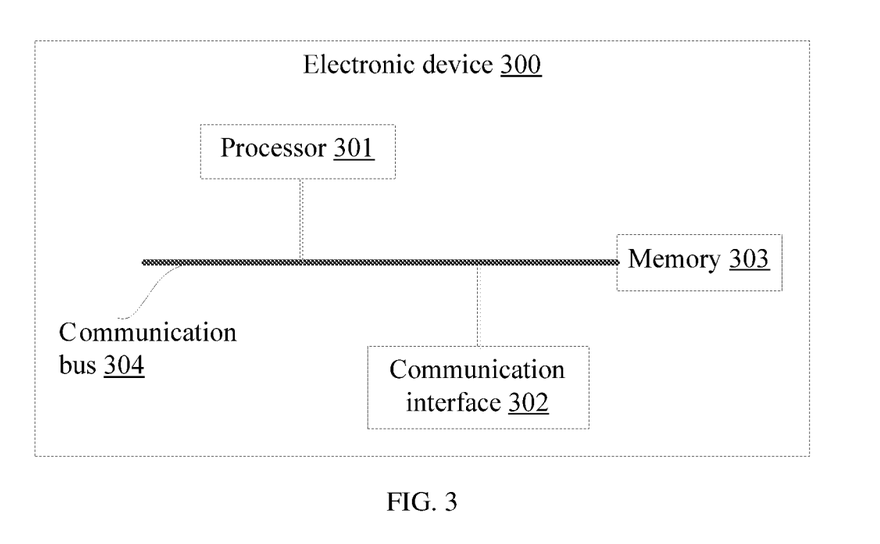
FIG. 3 is a schematic structural view of an electronic device according to an embodiment of the disclosure.

Referring to FIG. 3, it is a schematic structural view of an electronic device according to the embodiment of the disclosure. The electronic device includes a processor 301, a communication interface 302, a memory 303 and a communication bus 304. The processor 301, the communication interface 302 and the memory 303 are mutually communicated with one another via the communication bus 304.

The memory 303 is used for storing computer program(s);

The processor 301 is used for executing the computer program(s) stored in the memory 303, so as to carry out any of the blockchain-based electronic medical record sharing methods of the above embodiments.

The communication bus mentioned above in the electronic device can be peripheral component interconnect (PCI) bus or extended industry standard architecture (EISA) bus. The communication bus can be divided into an address bus, a data bus, a control bus and so on. For the convenience of illustration, only one thick line is used in the schematic structural view, but it does not mean that there is only one bus or one type of bus.

The communication interface is used for communication between the electronic device above and other devices.

The memory may include a random access memory (RAM) or a non-volatile memory (NVM), such as at least one disk memory. Optionally, the memory may also be at least one storage device far away from the aforementioned processor.

The aforementioned processor may be a general-purpose processor, including a Central Processing Unit (CPU), a Network Processor (NP), etc.; it can also be a Digital Signal Processing (DSP), an Application Specific Integrated Circuit (ASIC), Field-Programmable Gate Array (FPGA) or other programmable logic devices, discrete gate or transistor logic devices, discrete hardware components.

Through the above-mentioned electronic device, the public key and private key are generated by GRS code of finite field $F_q$, the electronic medical record abstract is obtained according to the electronic medical record, the electronic medical record abstract is processed by the private key to obtain the digital signature, the digital signature is encapsulated into the block, and the block is confirmed through the consensus mechanism and sent to the medical institution node. Based on blockchain technology and digital signature technology, the disclosure can ensure that the electronic medical record can be shared among various medical institutions without being tampered with. Moreover, the digital signature solution is highly feasible, which can reduce public key quantity, improve the signature efficiency, and further improve the security.

A digital signature method based on GRS code of the finite field is adopted in the disclosure. The solution provided by the embodiment of the disclosure is verified from correctness, feasibility, security, public key quantity and signature length of the digital signature.

(1) Correctness:

The verification of correctness is also to verify whether the signature succeeds. The correctness can be proved by proving that the to-be-verified electronic medical record abstract by decrypting the second error vector with public key is equal to the electronic medical record abstract obtained in the process of generating the signature. The specific process is as follows:

The public key is used to process the second error vector to obtain the to-be-verified electronic medical record abstract. The public key is obtained by performing a matrix multiplication operation on the inverse matrix of nonsingular matrix, a check matrix and transpose matrix of the transformation matrix, i.e. the above formula (2); the second error vector is obtained by performing a matrix multiplication operation on the first error vector and the inverse matrix of the inverse matrix of the private key, i.e. the above formula (4). The to-be-verified electronic medical record abstract is based on the product of a value of a corresponding row indexed according to the index $\alpha_j$ in each column of the public key $\vec{H}'$ and $c_j$, i.e., the above formula (6).

Therefore, by substituting the formula (2) and the formula (4) into the formula (6), it can be obtained that, $$y = \vec{S}^{-1} \cdot \vec{H} \cdot \vec{Q}^T \cdot \left(\vec{e} \cdot \vec{Q}^{-1}\right)^T \qquad (7)$$

By simplifying the formula (7), it can be obtained that:

$$y = \vec{S}^{-1} \cdot \vec{H} \cdot \vec{e}^T \qquad (8)$$

Due to $S'_x = \vec{H} \cdot \vec{e}^T$, it can be obtained from the formula (8) that:

$$y = \vec{S}^{-1} \cdot S'_x.$$

Where y represents the electronic medical record abstract to be verified, $\vec{S}^{-1}$ represents the inverse of a nonsingular matrix, $S'_x$ represents the to-be-decoded corrector.

The to-be-decoded corrector is obtained by a multiplication operation on the nonsingular matrix and the electronic medical record abstract, that is the above formula (3).

Therefore, according to the formula (3), it can be obtained that: $y = S_x$. That is, if $y = y'$, the verification succeeds, which means that the signature is correct.

(2) Feasibility:

Supposed that the total number of correctors of GRS codes based on the finite field $F_q$ is N, and $N = q^{n-k} = q^{2t} = q^{2mt}$, the number of correctors that can be used to decoded is M, and $$M = \sum_{i=0}^{t} \binom{n}{i} \times (q-1)^i,$$

therefore, the probability of successful attempts for the electronic medical record abstract $S_x$ is $$P = \frac{M}{N},$$

that is, the average number of attempts is $$Z = \frac{1}{P}.$$

The selection of the parameter pair (m, t) of GRS code signature based on the finite field $F_q$ should not only ensure that the average number of attempts is less than 10 million orders of magnitude, but also ensure that the selection of parameter pair cannot be too small.

Figure 4:
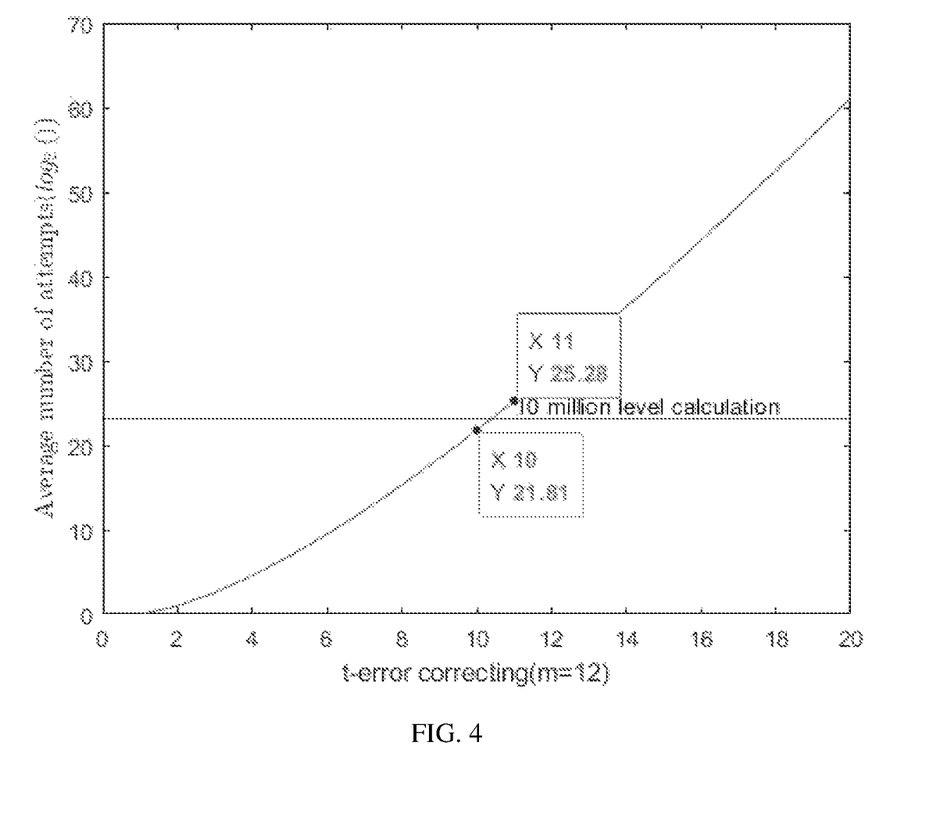
FIG. 4 is a simulation result diagram of feasibility of a signature method according to an embodiment of the disclosure.

Referring to FIG. 4, it is a simulation result diagram of the feasibility of the signature method provided by the embodiment of the disclosure. The diagram shows the relationship between the error correction capability t and the logarithm of the average number of attempts $\log_2 Z$. As illustrated in FIG. 4, the error correction capability t is proportional to the logarithm of the average number of attempts $\log_2 Z$, that is, the logarithm of the average number of attempts $\log_2 Z$ has an exponential relationship with the error correction capability t.

The horizontal line in FIG. 4 represents the calculation of tens millions of orders of magnitude, and the data x represents m and y represents $\log_2 Z$.

When the value of the error correction capability t is greater than 10, the average number of attempts will be too large. Therefore, it is more appropriate while the error correction capability t is less than or equal to 10.

Figure 5:
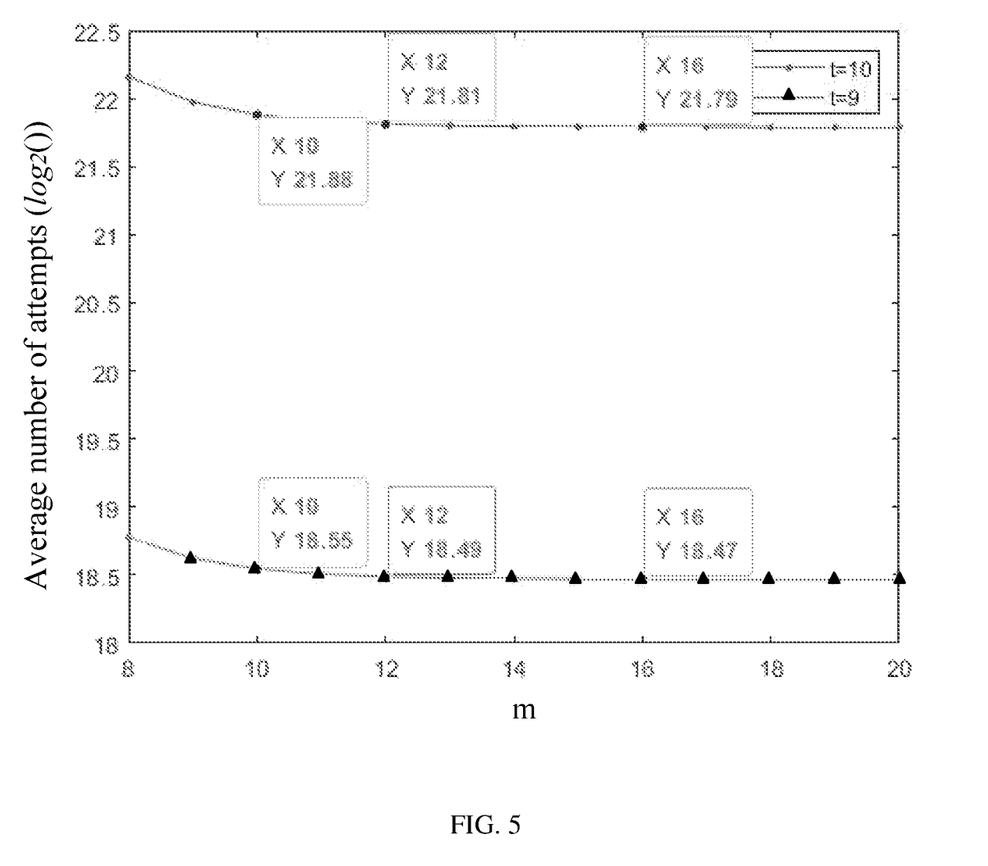
FIG. 5 is a simulation result diagram of feasibility under different error correction capabilities of a signature method according to an embodiment of the disclosure.

Referring to FIG. 5, it shows the simulation result of a feasibility of a signature method under different error correction capabilities. FIG. 5 shows a relationship between m and the logarithm of the average number of attempts when the error correction capability t is 9 and 10. In the diagram, x represents m and y represents $\log_2 Z$. As illustrated in FIG. 5, when $m \geq 12$, with the increase of m, $\log_2 Z$ tends to be stable with little change. When $m < 12$, the average number of attempts will increase. Therefore, it is more appropriate for m to be greater than or equal to 12.

In addition, two groups of data in Table 2 can be obtained according to FIG. 5.

TABLE 2

| (a) | | | | | | | |
|---|---|---|---|---|---|---|---|
| m (t = 10) | 6 | 8 | 10 | 12 | 14 | 16 | 18 |
| $\log_2 Z$ | 23.33 | 22.16 | 21.88 | 21.81 | 21.80 | 21.79 | 21.79 |
| (b) | | | | | | | |
| m (t = 9) | 6 | 8 | 10 | 12 | 14 | 16 | 18 |
| $\log_2 Z$ | 19.74 | 18.78 | 18.55 | 18.49 | 18.47 | 18.4703 | 18.47 |

It is known that the parameter pairs (m, t) used by CFS signature are (15, 10) and (16, 9). when the parameter pair is (15, 10), the logarithm of the average number of attempts of CFS signature is 27.7911, and that of GRS code signature based on the finite field $F_q$ is 21.7933; when the parameter pair is (16, 9), the logarithm of average number of attempts of CFS signature is 18.4691, and that of GRS code signature based on the finite field $F_q$ is 18.4703.

In comparison, under the two parameter pairs, the data of average number of attempts of CFS signature and GRS code signature based on the finite field $F_q$ are not different, so the GRS code digital signature method based on the finite field $F_q$ is feasible.

Figure 6:
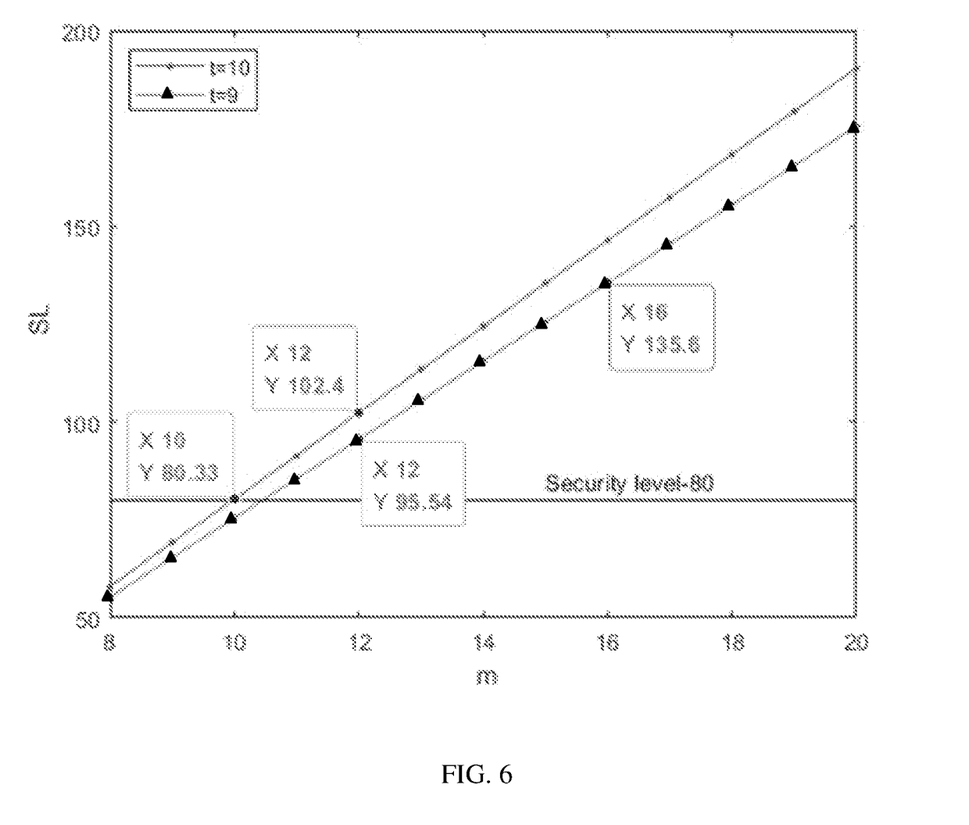
FIG. 6 is a simulation result diagram of a signature method under an ISD decoding attack according to an embodiment of the disclosure.

(3) Security:

Referring to FIG. 6, it shows the simulation result of the signature method under ISD decoding attack provided by the embodiment of the disclosure. FIG. 6 shows the relationship between m and security level SL in the case of ISD decoding attack.

Under ISD decoding attack, the security level coefficient is exponentially related to the product of m and t. Based on the above conditions, t is selected to be less than or equal to 10. That is, when t is determined, the larger m is, the higher the safety level coefficient is.

In the diagram data x is m, y is SL. As illustrated in FIG. 6, when the parameter pair of GRS code digital signature based on the finite field $F_q$ is (10,10), the security level SL can reach to 80, which has reached to a general security level. When the parameter pair is (16, 9), the security level SL exceeds 128.

Under ISD decoding attack, when the parameter pair is (15, 10), the security level coefficient SL of CFS signature is 76.89, and that of GRS code signature based on the finite field $F_q$ is 135.42; when the parameter pair is (16, 9), the security level coefficient SL of CFS signature is 76.92, and that of GRS code signature based on the finite field $F_q$ is 135.56.

In comparison, the GRS code signature based on the finite field $F_q$ provided by the embodiment of the disclosure has a higher security level coefficient under ISD decoding attack.

In addition, the GRS code signature based on the finite field $F_q$ provided by the embodiment of the disclosure can effectively resist discrimination attack, while the parameter selection of CFS signature under discrimination attack has defects.

(4) Public Key Quantity:

In the embodiment of the disclosure, the check matrix of GRS code is performed with Gauss elimination to obtain a row ladder matrix, that is the public key quantity of the public key $\vec{H}'$ is k·(n–k). Therefore, for GRS codes based on the finite field $F_q$, the public key quantity is k·(n–k)·$\log_2$ q.

Figure 7:
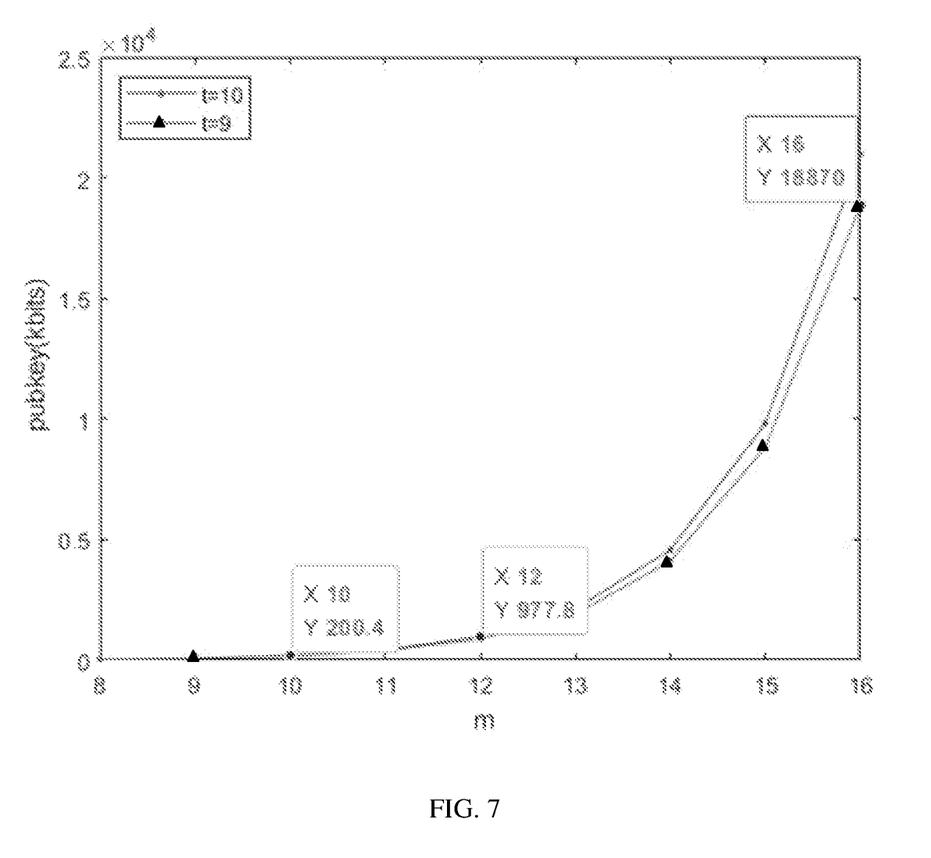
FIG. 7 is a simulation result diagram of a public key quantity under different error correction capabilities of a signature method according to an embodiment of the disclosure.

Referring to FIG. 7, it shows the simulation result of the public key quantity under different error correction capabilities of the signature method provided by the embodiment of the disclosure. FIG. 7 shows the relationship between m and the public key quantity when the error correction capability t is 9 and 10. In the diagram, x represents m and y represents k·(n–k)·$\log_2$ q. It can be seen from FIG. 7 that, the public key quantity is exponentially related to m, but the influence on the public key quantity is not obvious under different error correction capabilities t. Although the larger m is, the more secure the signature of GRS code based on the finite field $F_q$ is, which will also lead to a larger public key. Therefore, a more appropriate m is selected, which can make the security coefficient higher and the public key quantity smaller, for example, m is 10, 12, etc.

(5) Signature Length:

The length of the GRS code signature based on the finite field $F_q$ provided by the embodiment of the disclosure is 2m·$t_p$+$\log_2$ Z.

Table 3 shows the comparison of the average number of attempts, the security level, the public key quantity and the signature length between GRS code signature and CFS signature based on the finite field $F_q$ under two different parameter pairs.

Table 3 Parameters Comparison of GRS Code Signature and CFS Signature Based on the Finite Field Fq Under Different Parameter Pairs

| Parameter pair | | Average number of attempts | Security level (SL) | Public key quantity | Signature length (bits) |
|---|---|---|---|---|---|
| (15, 10) | This disclosure | 21.7939 | 135.4181 | 9823800 | 292 |
|  | CFS signature | 21.7911 | 76.8866 | 4892700 | 150 |
| (16, 9) | This disclosure | 18.4703 | 135.5624 | 18868608 | 275 |
|  | CFS signature | 18.4611 | 76.9210 | 9416448 | 144 |

As shown from table 3, under different parameter pairs, the security level coefficient of GRS code signature based on the finite field $F_q$ provided by the embodiment of the disclosure is higher than that of CFS signature, but the public key quantity and digital signature length are also larger.

Therefore, several groups of parameters of GRS code signature based on the finite field $F_q$ under different parameter pairs are selected for simulation. The results are shown in Table 4.

Table 4 Parameters of GRS Code Signature Based on the Finite Field Fq Under Different Parameter Pairs

| Parameter pair | Average number of attempts | Security level (SL) | Public key quantity | Signature length (bits) |
|---|---|---|---|---|
| (11, 9) | 18.5072 | 85.5239 | 401544 | 195 |
| (10, 10) | 21.8829 | 80.3254 | 200400 | 202 |
| (12, 10) | 21.8140 | 102.3972 | 977760 | 238 |

The GRS code signature based on the finite field $F_q$ provided by the embodiment of the disclosure can reduce the selection of parameter pairs, reduce the public key quantity and the length of signature on the premise of improving the security level coefficient.

Through the above verification, it is proved that the digital signature solution adopted in the disclosure has the effects of correctness, feasibility and security, as well as the reduction of public key quantity and signature length.

The foregoing content is a further detailed description of the disclosure in combination with the specific preferred embodiment, and it cannot be considered that the specific implementation of the disclosure is limited to these descriptions. For those of ordinary skill in the art of the disclosure, any simple deduction, modifications, equivalent substitutions, improvements, etc., made within the spirit and scope of the disclosure, should be included in the protection scope of the application.

What is claimed is:

1. A blockchain-based electronic medical record sharing method, adapted for a medical institution node, comprising steps of:

obtaining an electronic medical record from a preset database;

performing a Hash operation on the electronic medical record to generate a medical record abstract;

constructing a Generalized Reed-Solomon (GRS) code based on a finite field, comprising:

constructing the finite field; and constructing the GRS code with a code length of n, a dimensionality of k and an error correction capability of t according to the finite field, wherein n, k, and t are arbitrary positive integers;

generating a public key and a private key according to the GRS code, comprising:

selecting a nonsingular matrix of (n–k)×(n–k), a dense matrix of n×n having ranking z, and a sparse matrix of n×n in the finite field with an average row weight and an average column weight of x, z and x are natural numbers, z<n, and x<n;

performing a matrix addition operation on the dense matrix and the sparse matrix to obtain a transformation matrix;

performing a matrix multiplication operation on an inverse matrix of the nonsingular matrix, a check matrix of the GRS code of size (n–K)×n, and a transpose matrix of the transformation matrix to obtain the public key; and defining the private key as comprising the nonsingular matrix, the check matrix, the transformation matrix, and a decoding algorithm;

using the private key to process the electronic medical record abstract to thereby obtain a first digital signature;

decoding the first digital signature with the private key to obtain an error vector as a second digital signature;

decoding the first digital signature using the decoding algorithm and the transformation matrix to obtain a first error vector;

performing a matrix multiplication operation on the first error vector and an inverse matrix of the transformation matrix to obtain a second error vector, wherein a weight of the second error vector is less than or equal to the error correction capability t of the GRS code;

constructing an index pair of the second error vector and using the index pair as a second digital signature;

sending the second digital signature to a verification node for verification; and receiving a block confirmed by the verification node and adding the block to a blockchain structure maintained by the preset database.

2. The blockchain-based electronic medical record sharing method as claimed in claim 1, wherein the step of constructing a GRS code based on a finite field, comprises:

constructing the finite field, and constructing the GRS code with a code length of n, a dimensionality of k and an error correction capability of t according to the finite field, where n, k, and t are arbitrary positive integers and satisfy $$t = \left\lfloor \frac{n-k}{2} \right\rfloor.$$

3. The blockchain-based electronic medical record sharing method as claimed in claim 1, wherein the step of performing a Hash operation on the electronic medical record to generate a medical record abstract, comprises:

performing a first Hash operation on the electronic medical record; and performing a second Hash operation on a result obtained by the first Hash operation to obtain the medical record abstract.

4. The blockchain-based electronic medical record sharing method as claimed in claim 1, wherein the step of using the private key to process the electronic medical record abstract to thereby obtain a first digital signature, comprises:

performing a multiplication operation on the nonsingular matrix and the electronic medical record abstract to obtain the first digital signature.

5. The blockchain-based electronic medical record sharing method as claimed in claim 4, wherein the step of decoding the first digital signature with the private key to obtain an error vector as a second digital signature, comprises:

decoding the first digital signature with the decoding algorithm in combination with the transformation matrix of the private key to obtain a first error vector;

performing a matrix multiplication operation on the first error vector and an inverse matrix of the transformation matrix of the private key to obtain a second error vector, wherein a weight of the second error vector is less than or equal to a value of the error correction capability of the GRS code; and obtaining the second digital signature by using the second error vector.

6. A blockchain-based electronic medical record sharing method, adapted for a verification node, comprising steps of:

receiving a second digital signature from a medical institution node, wherein the second digital signature is obtained by the blockchain-based electronic medical record sharing method as claimed in claim 1;

obtaining the public key from the medical institution node and verifying the second digital signature according to the public key;

encapsulating the electronic medical record abstract into a block when the second digital signature is verified to be valid; and confirming the block through a consensus mechanism, and sending the block as confirmed to the medical institution node.

7. The blockchain-based electronic medical record sharing method as claimed in claim 6, wherein the step of obtaining the public key from the medical institution node and verifying the second digital signature according to the public key, comprises:

receiving the public key from the medical institution node, and processing the second digital signature by using the public key to obtain a to-be-verified medical record abstract;

obtaining the electronic medical record and performing a Hash operation on the electronic medical record to obtain a target medical record abstract; and comparing the to-be-verified medical record abstract with the target medical record abstract, determining that the verifying succeeds if the to-be-verified medical record abstract is the same as the target medical record abstract, otherwise determining that the verifying fails.

8. An electronic device comprising:

a processor;

a communication interface;

a memory; and a communication bus; wherein operatively connecting the processor, the communication interface and the memory are mutually communicated with one another via the communication bus; wherein the memory is configured for storing stores a computer program; computer-executable instructions, and wherein the processor is configured for executing the computer program stored in the memory to carry out to execute the instructions to perform a blockchain-based electronic medical record sharing method as claimed in claim 1, comprising:

obtaining an electronic medical record from a preset database;

performing a Hash operation on the electronic medical record to generate a medical record abstract;

constructing a GRS code based on a finite field, comprising:

(i) constructing the finite field; and (ii) constructing the GRS code with a code length n, a dimensionality k, and an error correction capability t satisfying $t=\lfloor(n-k)/2\rfloor$, where n, k, and t are positive integers;

generating a public key and a private key according to the GRS code, comprising:

(i) selecting a nonsingular matrix of size $(n-k)\times(n-k)$, a dense matrix of size $n\times n$ having rank z, and a sparse matrix of size $n\times n$ with average row weight and average column weight of x, where z and x are natural numbers, $z<n$, and $x<n$;

(ii) performing a matrix addition operation on the dense matrix and the sparse matrix to obtain a transformation matrix;

(iii) performing a matrix multiplication operation on an inverse matrix of the nonsingular matrix, a check matrix of the GRS code of size (n−k)×n, and a transpose of the transformation matrix to obtain the public key; and (iv) defining the private key as comprising the nonsingular matrix, the check matrix, the transformation matrix, and a decoding algorithm;

using the private key to process the medical record abstract to thereby obtain a first digital signature;

decoding the first digital signature using the decoding algorithm and the transformation matrix to obtain a first error vector;

performing a matrix multiplication operation on the first error vector and an inverse matrix of the transformation matrix to obtain a second error vector, wherein a weight of the second error vector is less than or equal to the error correction capability t of the GRS code;

constructing an index pair of the second error vector and using the index pair as a second digital signature;

decoding the first digital signature with the private key to obtain an error vector as a second digital signature;

sending the second digital signature to a verification node for verification; and receiving a block confirmed by the verification node and adding the block to a blockchain structure maintained by the preset database.

* * * * *